(12) United States Patent
Saidha et al.

(10) Patent No.: US 8,486,149 B2
(45) Date of Patent: Jul. 16, 2013

(54) EXPANDABLE INTERBODY FUSION IMPLANT

(75) Inventors: Sean Saidha, Oberdorf (CH); Michael White, Oberdorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 89 days.

(21) Appl. No.: 13/033,119

(22) Filed: Feb. 23, 2011

(65) Prior Publication Data

US 2012/0215313 A1 Aug. 23, 2012

(51) Int. Cl.
*A61F 2/44* (2006.01)
(52) U.S. Cl.
USPC .................................... 623/17.16; 623/17.11
(58) Field of Classification Search
USPC ........................................... 623/17.11–17.16
See application file for complete search history.

(56) References Cited

U.S. PATENT DOCUMENTS

| | | | |
|---|---|---|---|
| 4,759,769 A | 7/1988 | Hedman et al. | |
| 6,190,414 B1 * | 2/2001 | Young et al. | 623/17.15 |
| 6,193,757 B1 * | 2/2001 | Foley et al. | 623/17.16 |
| 6,582,467 B1 | 6/2003 | Teitelbaum et al. | |
| 6,953,477 B2 | 10/2005 | Berry | |
| 7,083,650 B2 | 8/2006 | Moskowitz et al. | |
| 7,678,148 B2 * | 3/2010 | Peterman | 623/17.11 |
| 7,862,616 B2 * | 1/2011 | Lechmann et al. | 623/17.11 |
| 2004/0133280 A1 | 7/2004 | Trieu | |
| 2008/0125865 A1 | 5/2008 | Abdelgany | |
| 2008/0243251 A1 | 10/2008 | Stad et al. | |
| 2008/0243255 A1 | 10/2008 | Butler et al. | |
| 2009/0054991 A1 | 2/2009 | Biyani et al. | |
| 2009/0076610 A1 * | 3/2009 | Afzal | 623/17.16 |
| 2009/0143859 A1 | 6/2009 | McClellan, III et al. | |
| 2009/0171389 A1 | 7/2009 | Sankaran | |
| 2010/0161062 A1 | 6/2010 | Foley et al. | |
| 2010/0185288 A1 | 7/2010 | Carls et al. | |
| 2010/0185291 A1 | 7/2010 | Jimenez et al. | |

FOREIGN PATENT DOCUMENTS

| | | |
|---|---|---|
| WO | WO 00/40179 | 7/2000 |
| WO | WO 01/56497 | 8/2001 |
| WO | WO 2004/039243 | 5/2004 |

OTHER PUBLICATIONS

International Patent Application No. PCT/US2011/025828: International Search Report and Written Opinion dated Nov. 4, 2011, 12 pages.

* cited by examiner

*Primary Examiner* — Pedro Philogene
(74) *Attorney, Agent, or Firm* — Woodcock Washburn LLP

(57) ABSTRACT

Disclosed is an expandable interbody fusion implant that is configured to have an initial configuration having a first footprint width suitable for being inserted into an intervertebral space and an expanded configuration having a second footprint width that is greater than the first footprint width. The implant may include a first body member and a second body member that is pivotally coupled to the first body member. The implant may be expanded using an inflatable balloon. The implant may be expanded bilaterally such that both body members rotate relative to the other or the implant may be expanded unilaterally such that one of the body members rotates relative to the other.

32 Claims, 9 Drawing Sheets

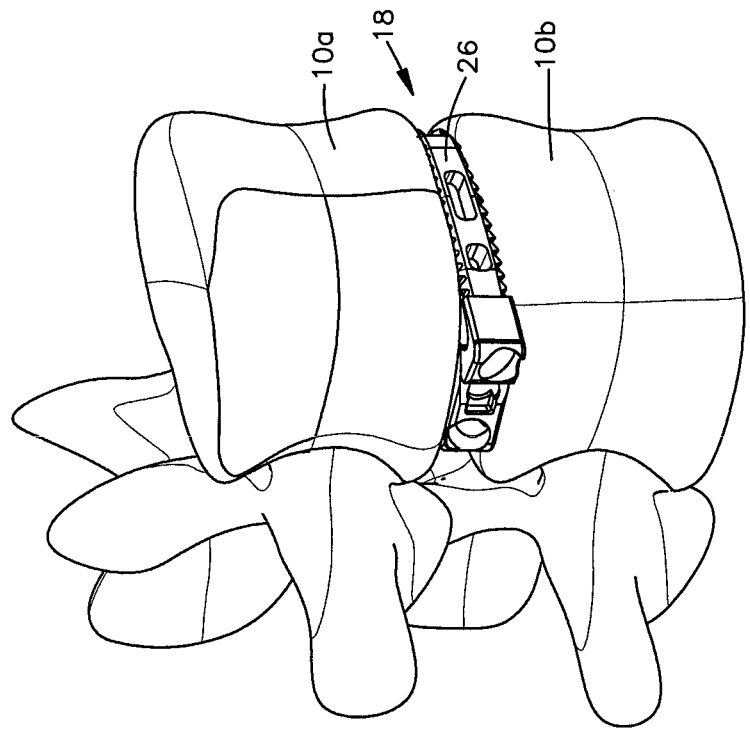
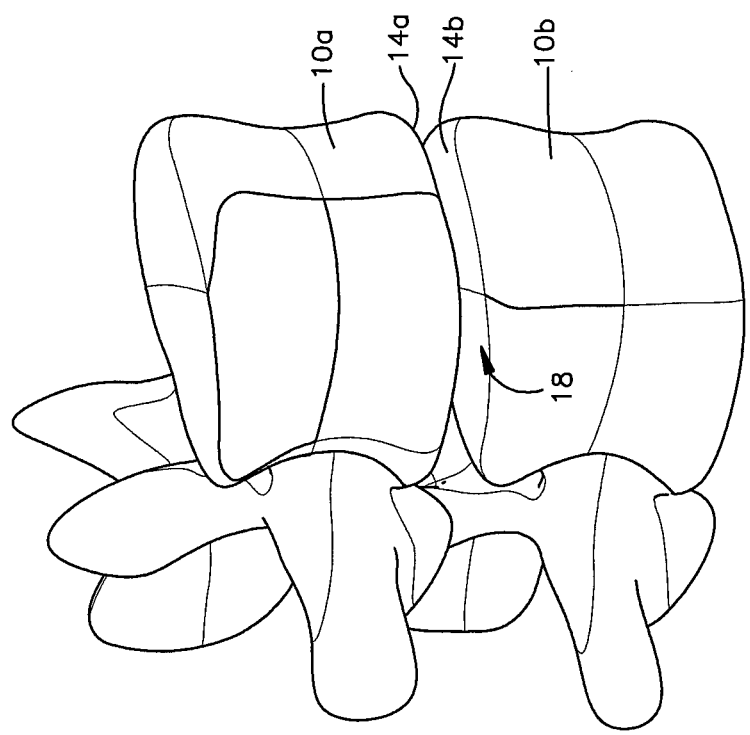

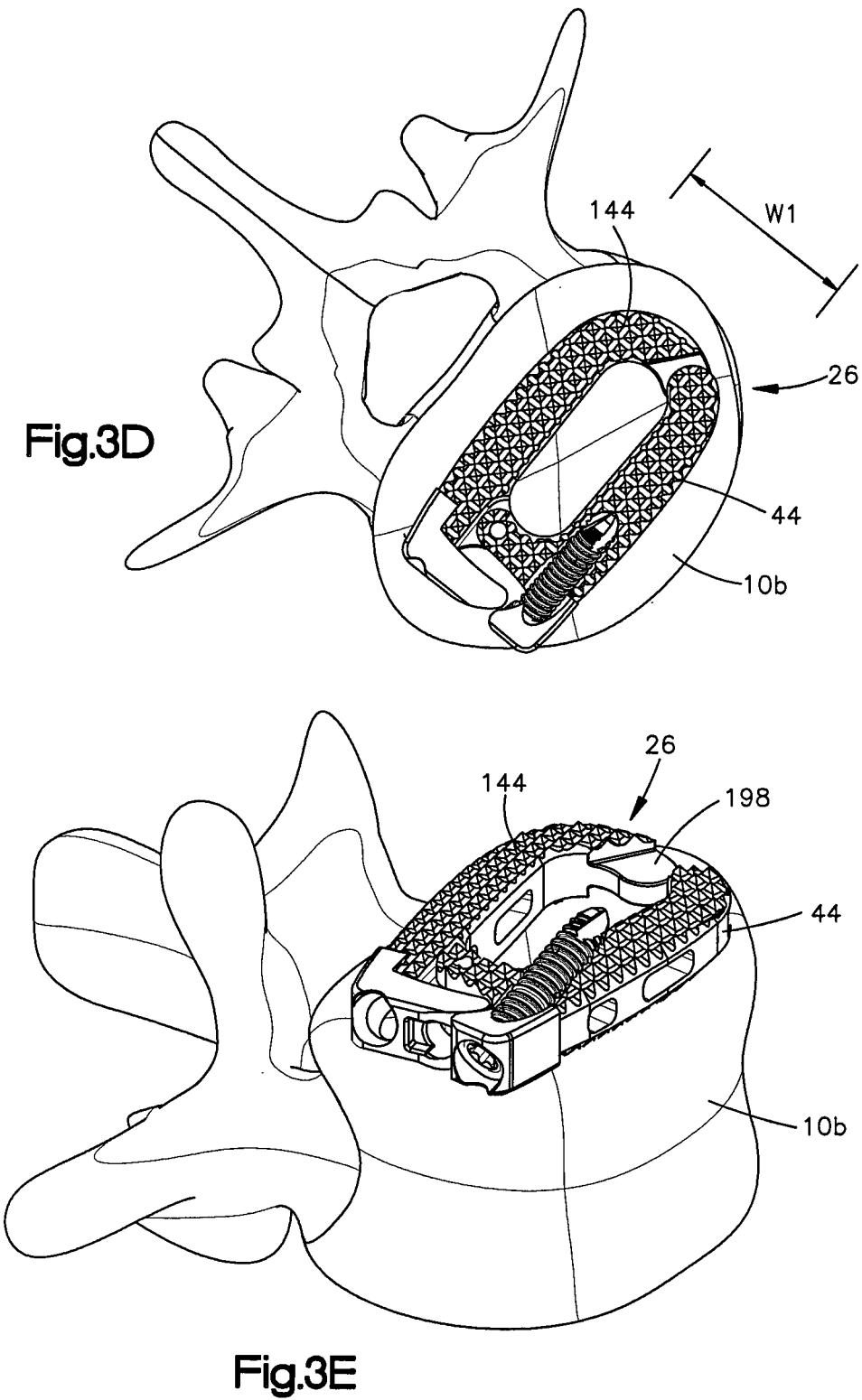

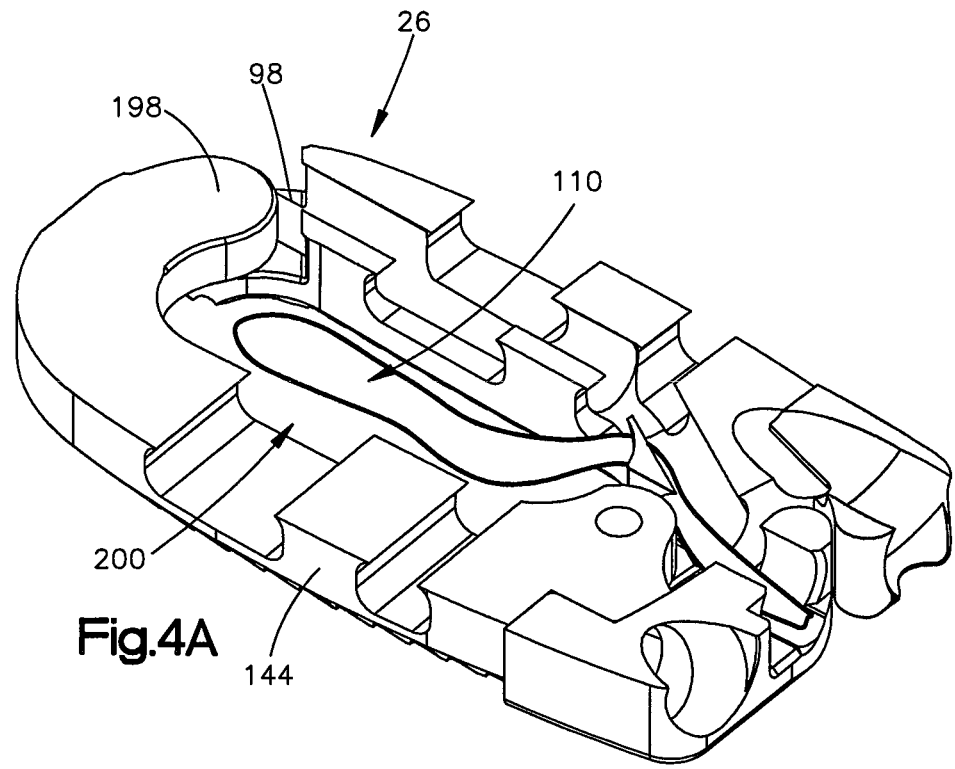
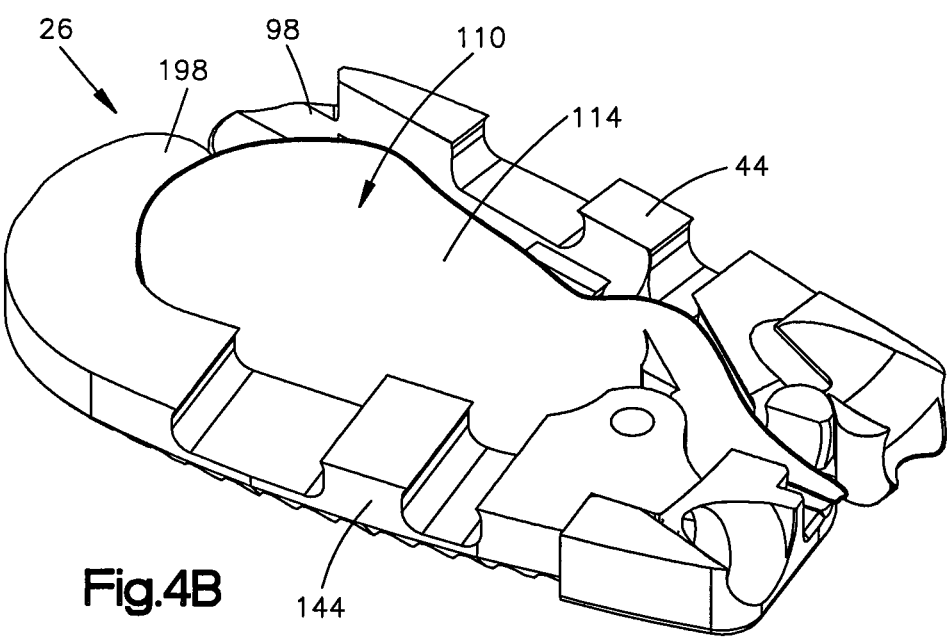

EXPANDABLE INTERBODY FUSION IMPLANT

BACKGROUND

Historically, complete removal of a disc from between adjacent vertebrae resulted in fusing the adjacent vertebrae together. This "interbody fusion" procedure, which is in use today, is a widely accepted surgical treatment for symptomatic lumbar and cervical degenerative disc disease (DDD). The aim of a spinal fusion is to relieve pain caused by a degenerated disc, restore anatomy (disc height and/or lordotic curvature), and immobilize the affected level (fusion). Such implants have mainly been inserted into lumbar and cervical intervertebral spaces between adjacent vertebral bodies through an anterior, antero-lateral (oblique), lateral, extraforaminal, transforaminal, or posterior surgical approach.

In most cases of interbody fusion, the main objective is to relieve pain while preventing iatrogenic injury. Moreover the interbody device should be stable and subsidence resistant. In order to prevent iatrogenic injury during interbody fusion, a minimally invasive approach offers an ideal solution, however, in order to provide stability and subsidence resistance, a large footprint is beneficial. Therefore, a compromise is generally required to achieve both.

While many minimally invasive interbody fusion devices are offered in a fixed shape, some are available that include an expandable footprint. These expandable devices, however, are not ideal and improvements are desired.

SUMMARY

Disclosed is an expandable interbody fusion implant that is configured to have an initial unexpanded configuration having a first footprint width suitable for being inserted into an intervertebral space defined by a pair of adjacent vertebral bodies, and an expanded configuration having a second footprint width that is greater than the first footprint width. The implant may be expanded from the initial configuration to the expanded configuration either bilaterally or unilaterally.

In one embodiment the implant may include a first body member and a second body member that is pivotally coupled to the first body member about a pivot axis. The first body member may have a first cage body and the second body member hay have a second cage body. The implant may also include a channel that extends at least partially through at least one of the first and second cage bodies, the channel configured to receive an inflatable balloon. The second body member may be configured to be adjacent the first body member, such that expansion of the inflatable balloon biases the first and second body members away from each other, thereby causing the implant to move from the initial configuration to the expanded configuration.

In another embodiment the implant may include a first body member and a second body member that is pivotally coupled to the first body member. The first body member may be configured to be braced against a vertebral surface. The first body member may include a first elongate cage body. The first elongate cage body may define superior and inferior bone engaging surfaces. The first elongate cage body may have a free end. The second body member may include a second elongate cage body. The second elongate cage body may define superior and inferior bone engaging surfaces. The second elongate cage body may have a free end. The implant may be configured to receive an expandable element, such that when the expandable element is expanded at least the second body member pivots with respect to the first body member so as to move at least the free end of the second body member relative to the free end of the first body member and expand the implant to the expanded configuration.

Also disclosed is a method of implanting an intervertebral implant into an intervertebral space that is defined by a superior vertebral body and an inferior vertebral body that are opposed in a transverse direction. According to the method, an expandable implant may be inserted into the intervertebral space. The implant may have a first width during insertion. The implant may include a first body member, and a second body member pivotally coupled to the first body member. The first and second body members may each include a fixation element receiving aperture. An inflatable balloon may then be positioned within the implant. By inflating the balloon, the implant may expand in a direction that is substantially perpendicular to the transverse direction. The implant may expand to a second width that is greater than the first width.

BRIEF DESCRIPTION OF THE DRAWINGS

The foregoing summary, as well as the following detailed description of illustrative embodiments of the interbody fusion implant of the present application, will be better understood when read in conjunction with the appended drawings. For the purposes of illustrating the interbody fusion implant of the present application, there is shown in the drawings illustrative embodiments. It should be understood, however, that the application is not limited to the precise arrangements and instrumentalities shown. In the drawings:

FIG. 1A is a side perspective view of a pair of vertebral bodies separated by an intervertebral space;

FIG. 1B is a side perspective view of an expandable intervertebral implant in accordance with one embodiment, the implant inserted into the intervertebral space shown in FIG. 1A, the implant expandable between an unexpanded configuration having a first footprint width, and an expanded configuration having a second footprint width that is greater than the first footprint width;

FIG. 3D is a top plan view of the implant shown in FIG. 3C;

FIG. 3E is a side perspective view of the implant shown in FIG. 3D, after the implant has been expanded to its expanded configuration;

FIG. 4A is a cross-sectional side perspective view of an expandable intervertebral implant in accordance with another embodiment, the implant including a first body member and a second body member that are spaced apart so as to define a cavity therebetween, the cavity receiving an expandable element; and FIG. 4B is a cross-sectional side perspective view of the implant shown in FIG. 4A, with the expandable element in an expanded configuration to thereby expand the implant to its expanded configuration.

DETAILED DESCRIPTION

Figure 2A:
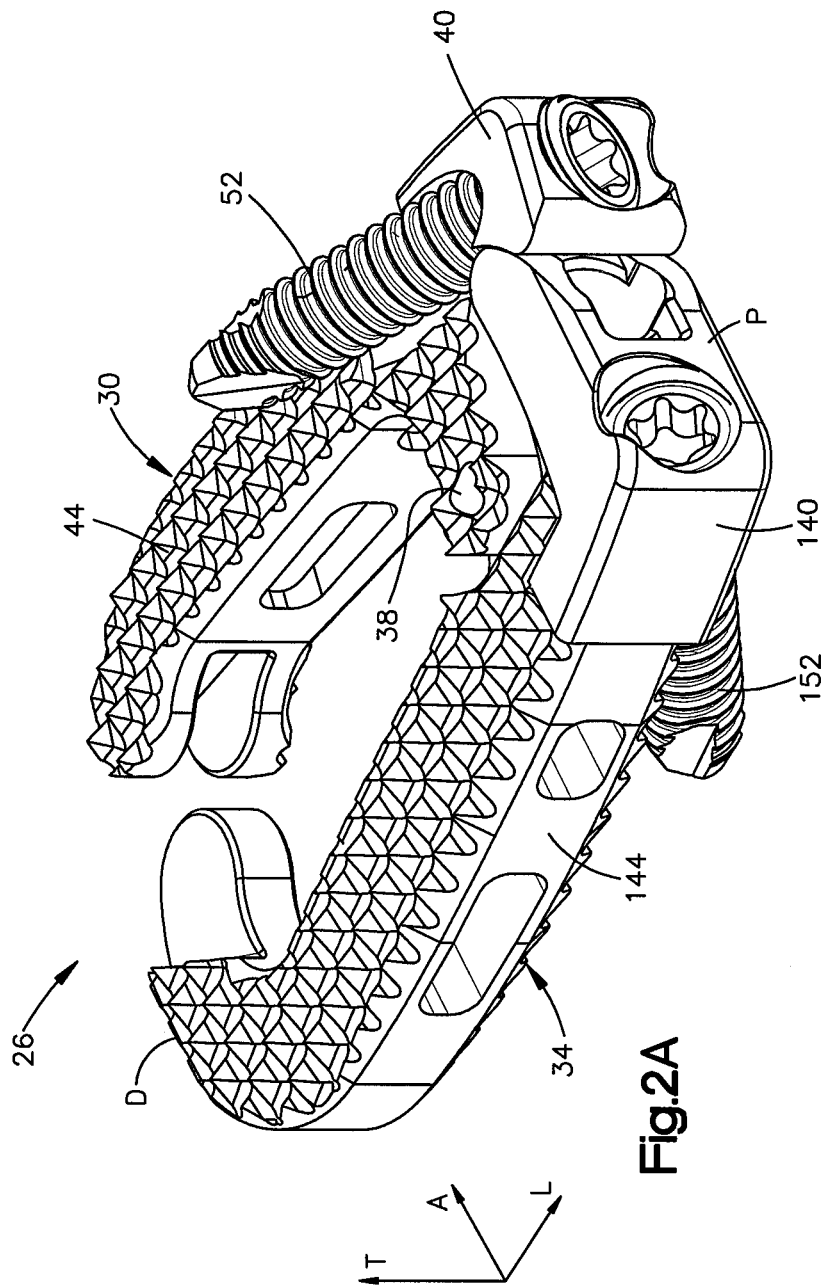
FIG. 2A is a side perspective view of the expandable intervertebral implant shown in FIG. 1B, the implant including a first body member and a second body member pivotally coupled to the first body member, each body member having a plate and a cage body.

Referring to FIGS. 1A and 1B, a superior vertebral body 10a defines a superior vertebral surface 14a of an intervertebral space 18, and an adjacent inferior vertebral body 10b defines an inferior vertebral surface 14b of the intervertebral space 18. Thus, the intervertebral space 18 is disposed between the vertebral bodies 10a-b. The vertebral bodies 10a-b can be anatomically adjacent vertebral bodies, or remaining vertebral bodies after a vertebral body has been removed from a location between the vertebral bodies 10a-b. As illustrated, the intervertebral space 18 is illustrated after a discectomy, whereby the disc material has been removed or at least partially removed to prepare the intervertebral space 18 to receive an intervertebral implant 26, as shown in FIG. 1B, that can achieve height restoration. The intervertebral space 18 can be disposed anywhere along the spine as desired, including at the lumbar, thoracic, and cervical regions of the spine.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

The implant 26 is described herein as extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. It should be appreciated that while the longitudinal and lateral directions are illustrated as extending along a horizontal plane, and that the transverse direction is illustrated as extending along a vertical plane, the planes that encompass the various directions may differ during use. For instance, when the implant 26 is implanted into an intervertebral space, such as the intervertebral space 18, the transverse direction T extends vertically generally along the superior-inferior (or caudal-cranial) direction, while the horizontal plane defined by the longitudinal direction L and lateral direction A lies generally in the anatomical plane defined by the anterior-posterior direction, and the medial-lateral direction. Accordingly, the directional terms "vertical" and "horizontal" are used to describe the implant 26 and its components as illustrated merely for the purposes of clarity and illustration.

Referring now to FIGS. 1B and 2A-2E, the interbody expandable implant 26 is configured to be positioned within an at least partially cleared out disc space, such as the disc space 18 disposed between the superior vertebral body 10a and the inferior vertebral body 10b. The implant is elongate in the longitudinal direction L and defines a distal end D and a proximal end P. The implant 26 is expandable between a first initial unexpanded configuration having a first footprint width, and a second expanded configuration having a second width that is greater than the first width. The implant 26 may be implanted while in the unexpanded configuration so as to provide a minimally invasive approach for the procedure. Once positioned within the intervertebral space, the implant 26 may be expanded in situ to its expanded configuration so as to provide an adequate footprint for an interbody fusion device. The expanded implant 26 may achieve improved stability and may reduce subsidence risk. The implant 26 can be formed entirely from or partially from a range of biocompatible materials or combinations of materials, including polymers, such as PEEK, porous PEEK, carbon fiber-reinforced PEEK, titanium and titanium alloys, stainless steel, ceramic, polylactic acid, tantalum, and magnesium, or even allograft bone.

As shown in FIGS. 2A-2E, the implant 26 includes a first body member 30 and a second body member 34 that is pivotally coupled to the first body member 30 at a hinge 38. At least one of the first body member 30 and the second body member 34 may rotate about the hinge 38 relative to the other to thereby expand the implant 26 to its expanded configuration. As shown, the first and second body members 30 and 34 may rotate in the horizontal plane. That is, after the implant 26 has been implanted into an intervertebral space that is defined between adjacent vertebral bodies that are opposed in the transverse direction T, the first and second body members 30 and 34 may rotate in a plane that is substantially perpendicular to the transverse direction T, so at increase the overall footprint of the implant 26. The implant 26 is configured such that both body members 30 and 34 may rotate so as to provide bilateral expansion of the implant. The implant 26 may also be configured such that only one of the body members 30 and 34 rotates relative to the other so as to provide unilateral expansion. Such unilateral expansion may be desired if the implant is positioned anterior using a lateral approach. Because in such a case the major vessels (aorta and vena cava) reside anterior to the vertebral column, a bilateral expansion may damage the vessels. Therefore, one of the body members 30 and 34 may be affixed to a vertebra prior to expansion of the implant 26 to thereby allow for unilateral expansion of the implant and prevent any damage to the vessels.

Figure 2B:
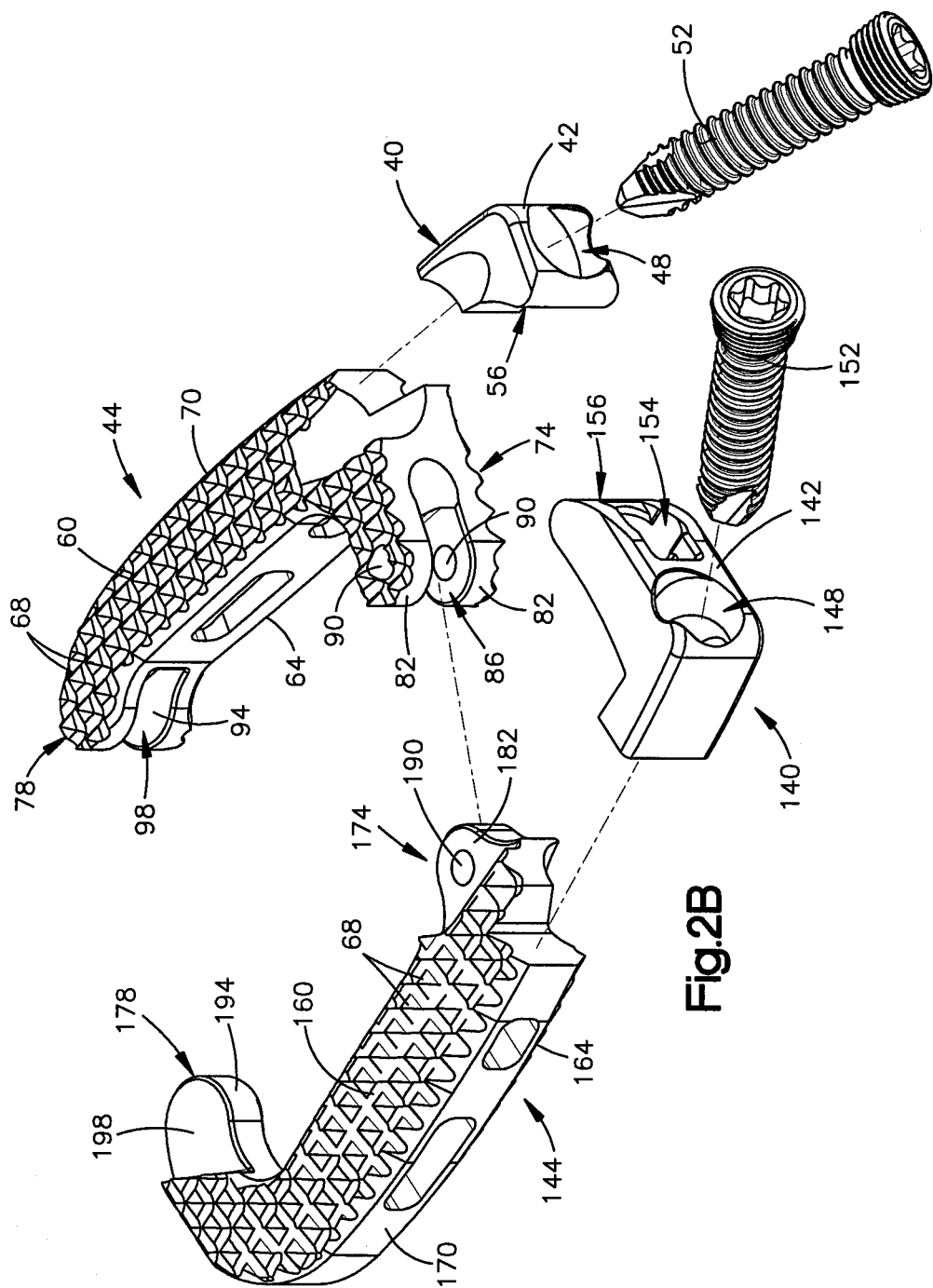
FIG. 2B is a an exploded view of the implant shown in FIG. 2A.
Figure 2C:
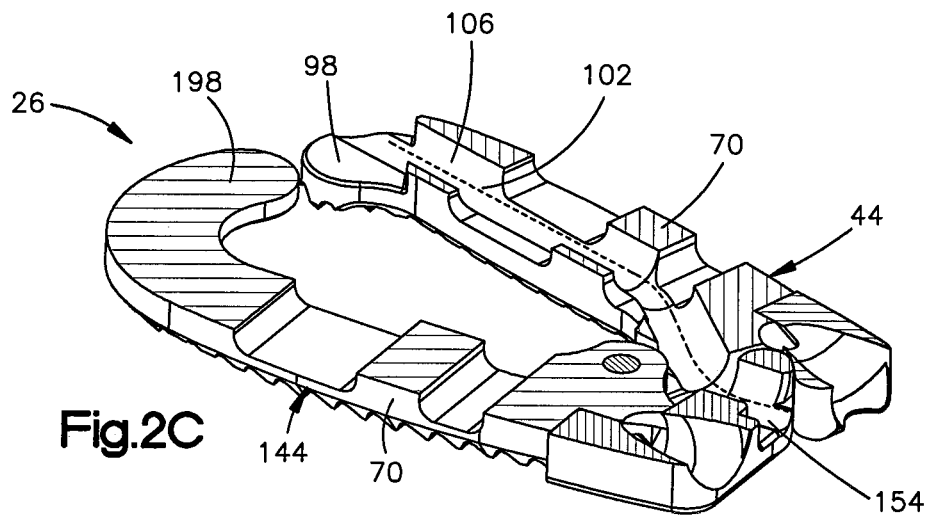
FIG. 2C is a cross-sectional side perspective view of the implant shown in FIG. 2A.

As best shown in FIGS. 2B and 2C, the first body member 30 includes a first plate 40, and a first cage body 44 that is coupled to the first plate 40. In particular, the first plate 40 is coupled to a proximal end of the first cage body 44. While the first plate 40 and the first cage body 44 are shown as separate components that are coupled together, it should be understood that the first plate 40 and the first cage body 44 may be integrally formed as one piece.

As best shown in FIG. 2B, the first plate 40 includes a front face member 42 that defines a fixation element receiving aperture 48 that extends therethrough from a front side to a back side at an upward angle. The fixation element receiving aperture 48 may define internal threads that are configured to engage external threads defined by a fixation element, such as bone screw 52, as the bone screw 52 is inserted into the fixation element receiving aperture 48. The bone screw 52 is configured to engage the superior vertebral body 10a once it is fully inserted to thereby brace or otherwise affix the first body member 30 to the vertebral body. The fixation element receiving aperture 48 may be fully enclosed as shown in the illustrated embodiment, or the fixation element receiving aperture 48 may be partially enclosed to thereby define for example a semi-circle. The fixation element receiving aperture 48 may be configured to receive a fixation element other than the bone screw 52. For example the fixation element receiving aperture 48 may be configured to receive blades or nails. Therefore, the fixation element receiving aperture 48 may be void of threads. Moreover, it should be understood that the first body member may be configured to be braced against the vertebral wall of the vertebral body using structure other than fixation elements. For example, the first body member 30 may be toothed so as to not allow the first body member 30 to rotate when the implant is inserted.

As shown in FIG. 2B, the first plate 40 also defines a curved internal surface 56 that is generally concave. As shown, the curved internal surface 56 is positioned such that it is adjacent the second body member 34. As will be discussed, the curved internal surface 56 allows the first body member 30 to rotate relative to the second body member 34 without substantial interference from the second body member 34.

As shown in FIGS. 2A and 2B, the first cage body 44 is elongate in the longitudinal direction L. The first cage body 44 defines an upper or superior or outer transverse bone engagement or contacting surface 60 configured to contact the superior vertebral body 10a, and a lower or inferior or outer transverse bone engagement or contacting surface 64 configured to contact the inferior vertebral body 10b. Both outer contacting surfaces 60 and 64 may include teeth 68 that are configured to engage the superior and inferior vertebral bodies 10a and 10b. As shown, the teeth 68 may be aligned in arcs with the centre of these arcs being proximate to the hinge 38.

As shown in FIG. 2B, the first cage body 44 includes an elongate body portion 70 that extends in the longitudinal direction L, and a first joint 74 that extends proximally from the elongate portion 70 and at least partially toward the second body member 34. In the embodiment shown, the joint 74 extends substantially perpendicularly from the elongate portion 70 toward the second body member 34. As shown, the cage body 44 also includes a free end 78 that extends distally from the elongate body portion 70 and at least partially toward the second body member 34. Therefore, because both the first joint 74 and the free end 78 at least partially extend toward the second body member 34, the first cage body 44 generally defines a C-shaped structure.

As shown, the first joint 74 includes a pair of plates 82 that are spaced apart so as to define a gap 86 between the two plates 78. Each plate 82 defines an aperture 90 that extends completely therethrough in the transverse direction T. As shown, each aperture 90 is aligned and is configured to receive a pin 94 as shown in FIG. 2C.

The free end 74 of the first cage body 44 defines a first mating feature 94. As shown, the first mating feature 94 includes a recess 98 that extends into the curved portion of the free end 74. The recess 98 is configured to receive a mating feature that is defined by the second body member 34 when the implant 26 is in an unexpanded configuration.

Figure 2D:
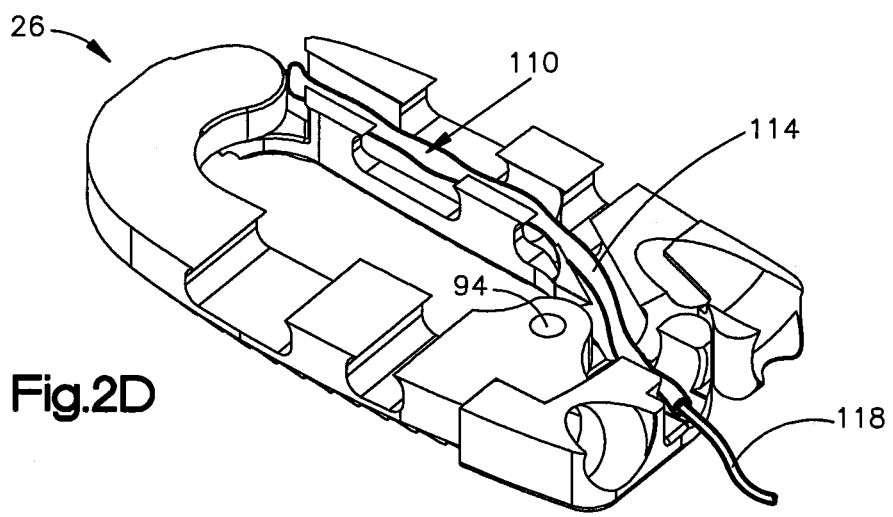
FIG. 2D is a cross-sectional side perspective view of the implant shown in FIG. 2C, the implant receiving an expandable element in a channel defined by the first body member.
Figure 2E:
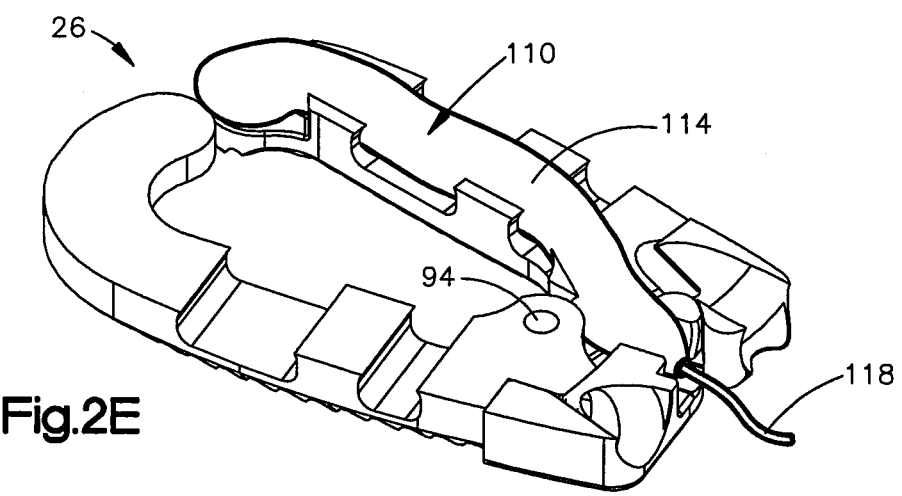
FIG. 2E is a cross-sectional side perspective view of the implant shown in FIG. 2D, with the expandable element in an expanded configuration to thereby expand the implant to its expanded configuration.

As best shown in FIG. 2C, the first body member 30 also defines a channel 102 that extends longitudinally through the first body member 30. That is, the channel 102 extends at least partially through the first joint 74, through the elongate body portion 70, and into the recess 94 defined by the free end 78. A shown, the channel 102 defines a non-linear path 106 from a proximal end of the implant 26 to the distal end of the implant 26. As shown in FIGS. 2D and 2E, the channel 102 is configured to receive an expandable element 110 so as to guide the expandable element 110 along the path 106 toward the recess 98. The expandable element 110 is configured to expand the implant 26 to its expanded configuration when the expandable element 110 has been activated. In the embodiment shown, the expandable element 110 is an inflatable balloon 114, that may be inflated by injecting air or some other fluid into a tube 118 that is coupled to a proximal end of the balloon 114. It should be understood, however, that the expandable element 110 is not limited to inflatable balloons and that other devices or materials may be used to expand the implant 26.

As best shown in FIGS. 2B and 2C, the second body member 34 includes a first plate 140, and a second cage body 144 that is coupled to the second plate 140. In particular, the second plate 140 is coupled to a proximal end of the second cage body 144. While the second plate 140 and the second cage body 144 are shown as separate components that are coupled together, it should be understood that the second plate 140 and the second cage body 144 may be integrally formed as one piece.

As best shown in FIG. 2B, the second plate 140 includes a front face member 142 that defines a fixation element receiving aperture 148 that extends therethrough from a front side to a back side at a downward angle. The fixation element receiving aperture 148 may define internal threads that are configured to engage external threads defined by a fixation element, such as bone screw 152, as the bone screw 152 is inserted into the fixation element receiving aperture 148. The bone screw 152 is configured to engage the inferior vertebral body 10b once it is fully inserted to thereby brace or otherwise affix the second body 34 against the vertebral body. The fixation element receiving aperture 148 may be fully enclosed as shown in the illustrated embodiment, or the fixation element receiving aperture 148 may be partially enclosed to thereby define for example a semi-circle. The fixation element receiving aperture 148 may be configured to receive a fixation element other than the bone screw 152. For example the fixation element receiving aperture 148 may be configured to receive blades or nails. Therefore, the fixation element receiving aperture 148 may be void of threads. Moreover, it should be understood that the second body member 34 may be configured to be braced against the vertebral wall of the vertebral body using structure other than fixation elements. For example, the second body member 34 may be toothed so as to not allow the second body member 34 to rotate when the implant is inserted.

As shown, the front face member 142 also defines a holding aperture 154 that extends therethrough adjacent to the fixation element receiving aperture 148. The holding aperture 154 is configured to receive an insertion tool so as to couple the implant 26 to the insertion tool for insertion of the implant 26 into the intervertebral space 18. The holding aperture 154 may include internal threads that are configured to engage external threads defined by the insertion tool to thereby securely couple the implant 26 to the insertion tool during insertion. As shown, the holding aperture 154 may also be substantially aligned with the channel 102. Therefore, the expandable element 110 may be inserted into the channel 102 through the holding aperture 154 as shown in FIGS. 2D and 2E.

As shown in FIG. 2B, the second plate 140 also defines a curved external surface 156 that is generally convex. As shown, the curved external surface 156 is positioned such that it is adjacent the curved surface 56 of the first body member 30. The curved surfaces 56 and 156 correspond to each other such that as the first body member 30 rotates relative to the second body member 34 the first and second plates 40 and 140 can slide past each without substantial interference.

As shown in FIGS. 2A and 2B, the second cage body 144 is elongate in the longitudinal direction L. The second cage body 144 defines an upper or superior or outer transverse bone engagement or contacting surface 160 configured to contact the superior vertebral body 10a, and a lower or inferior or outer transverse bone engagement or contacting surface 164 configured to contact the inferior vertebral body 10b. Both outer contacting surfaces 160 and 164 may include teeth 68 that are configured to engage the superior and inferior vertebral bodies 10a and 10b. As shown, the teeth 68 may be aligned in arcs with the centre of these arcs being proximate to the hinge 38.

As shown in FIG. 2B, the second cage body 144 includes an elongate body portion 170 that extends in the longitudinal direction L, and a second joint 174 that extends proximally from the elongate body portion 170 and at least partially toward the first body member 30. In the embodiment shown, the joint 174 extends substantially perpendicularly from the elongate body portion 170 toward the first body member 30. As shown, the cage body 144 also includes a free end 178 that extends distally from the elongate body portion 170 and at least partially toward the first body member 30. Therefore, because both the first joint 174 and the free end 178 at least partially extend toward the first body member 30, the second cage body 144 generally defines a C-shaped structure.

As shown, the second joint 174 includes a plate 182 that is configured to engage the gap 86 defined between the two plates 78 of the first joint 74. The plate 182 defines an aperture 190 that extends completely therethrough in the transverse direction T. As shown, the aperture 190 is configured to align with the apertures 90 of the first joint 74 when the plate 178 is received in the gap 86. The apertures 90 and 190 should align so that the pin 94 can engage each aperture 90 and 190 to thereby define the hinge 38. As shown in FIG. 2C, the hinge 38 defines a pivot axis that extends in the transverse or caudal-cranial direction. Therefore, at least one of the first body member 30 and the second body member 34 may rotate about the rotation axis in the horizontal plane defined by the longitudinal and lateral directions to thereby increase the overall footprint of the implant 26. It should be understood that the joints 74 and 174 may part of either the first body member 30 or the second body member 34. Moreover, the hinge 38 may be defined by structure other than the joints 74 and 174. For example, the first body member 30 and the second body member 34 may integral parts that are connected by an integral hinge 38 that allows at least one of first body member 30 and the second body member 34 to rotate relative to the other.

The free end 174 of the second cage body 144 defines a second mating feature 194. As shown, the second mating feature 194 includes a protrusion 198 that extends toward the recess 98 of the first body member 30. The second mating feature 194 is configured to mate with the first mating feature 94 when the implant 26 is in an unexpanded configuration. In particular, the protrusion 198 is configured to engage or otherwise extend into the recess 94 of the first body member 30 when the implant 26 is in an unexpanded configuration. As shown in FIG. 2D, when the implant 26 is in its unexpanded configuration, the first cage body 44 and the second cage body 144 (or at least their elongate body portions 70 and 170) are spaced apart such that a cavity 200 is defined between the elongate body portions 70 and 170. As shown, the cavity 200 is generally oval shaped and the overall implant 26 generally defines an oval shaped ring when the implant 26 is in an unexpanded configuration. Though it should be understood that the cavity 200 or at least the implant 26 may include other shapes as desired when the implant 26 is in its unexpanded configuration.

As shown in FIGS. 2D and 2E, the expandable element 110 may be inserted through the holding aperture 154 and into the channel 102 until a at least a portion of the expandable element 110 is within the recess 98 of the first body member 30 and adjacent to the protrusion 198. When the expandable element 110 is activated, the expandable element 110 will contact and apply a force to the protrusion 198 thereby causing at least one of the first body member 30 and the second body member 34 to rotate about the hinge 38. As the body members 30 and 34 rotate, the protrusion 198 recedes from the recess 98 such that the free ends 74 and 174 of the body members 30 and 34 move away from each other. The free ends 74 and 174 can be said to move away from each other if the protrusion 198 is completely disengages from the recess 98 or if the protrusion 198 partially disengages from the recess 98 so long as the protrusion 198 at least partially recedes from the recess 98.

Figure 3A:
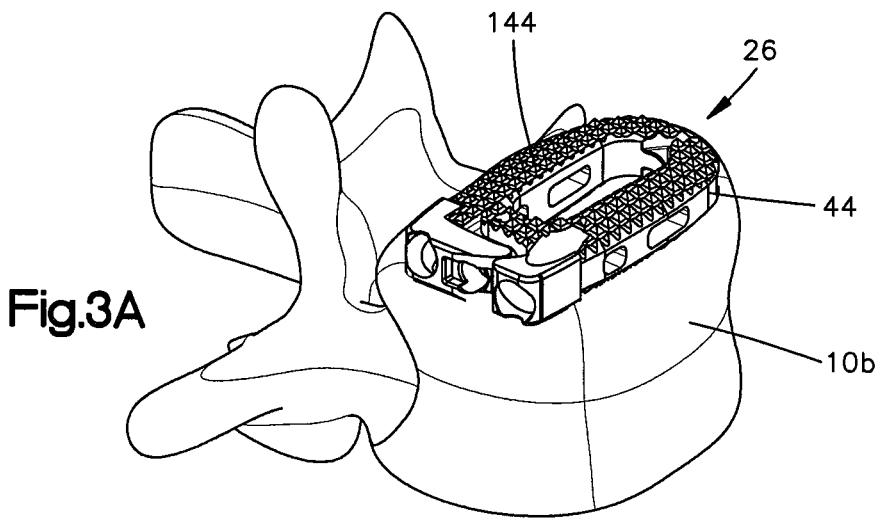
FIG. 3A is a side perspective view of the implant shown in FIG. 2A positioned in the intervertebral space while in the unexpanded configuration, the superior vertebral body is removed for clarity.
Figure 3B:
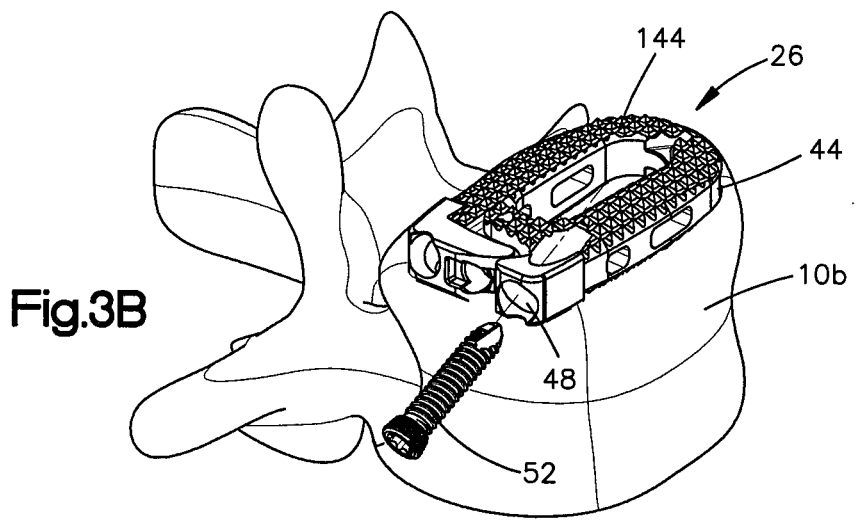
FIG. 3B is a side perspective view of a first fixation element being inserted into a first fixation element receiving aperture of the first body member of the implant shown in FIG. 3A.
Figure 3C:
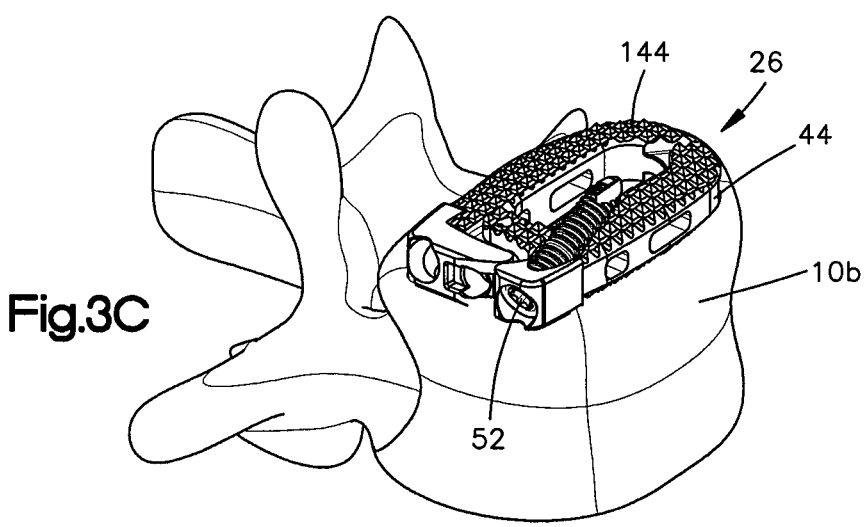
FIG. 3C is a side perspective view of the first fixation element fully inserted into the first fixation element receiving aperture of the implant so as to affix the first body member of the implant to the superior vertebral body.

In operation and in reference to FIGS. 3A-3I, the implant 26 may be inserted into the intervertebral space 18 while in an unexpanded. As best shown in FIG. 3D, the implant 26 may have an initial insertion or otherwise first width W1 when the implant 26 is being inserted into the intervertebral space 18. The initial width W1 may be narrow enough to allow for a minimally invasive approach to thereby reduce damage to the patient. Once the implant 26 has been inserted into the intervertebral space 18, the first bone screw 52 may be inserted into the fixation element receiving aperture 48 of the first body member 30 and into the superior vertebral body 10a, as shown in FIGS. 3B-3D. At this point the first body member 30 may be securely fixed to the superior vertebral body 10a.

Figure 3F:
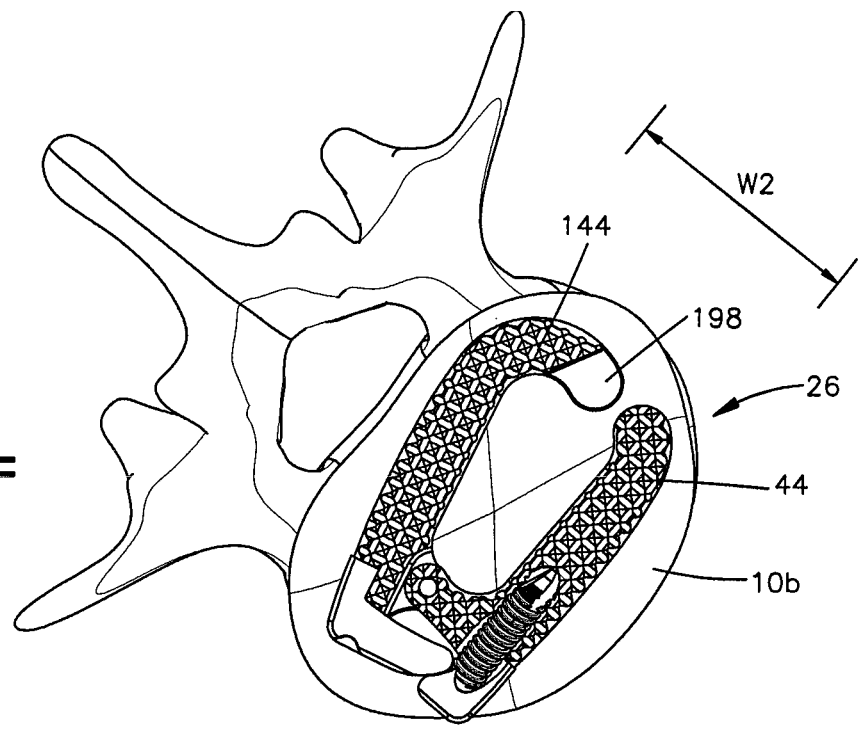
FIG. 3F is a top plan view of the implant shown in FIG. 3E.

As shown in FIGS. 3E and 3F, the expandable element 110 then be inserted through the holding aperture 154 and into the channel 102 so that at least a portion of the expandable element is proximate to the mating features 94 and 194. The expandable element 110 may then be activated or otherwise expanded so as to apply a force to the mating feature 194 to thereby cause the second body member 34 to rotate relative to the first body member 30 about the hinge 38 and expand the implant 26 to its expanded configuration. As best shown in FIG. 3F, the implant 26 may have an expanded or otherwise second width W2 that is greater than the first width W1 when the implant 26 is in the expanded configuration. As shown, when in the expanded configuration, the implant 26 has a greater footprint to thereby increase stability of the implant.

Figure 3G:
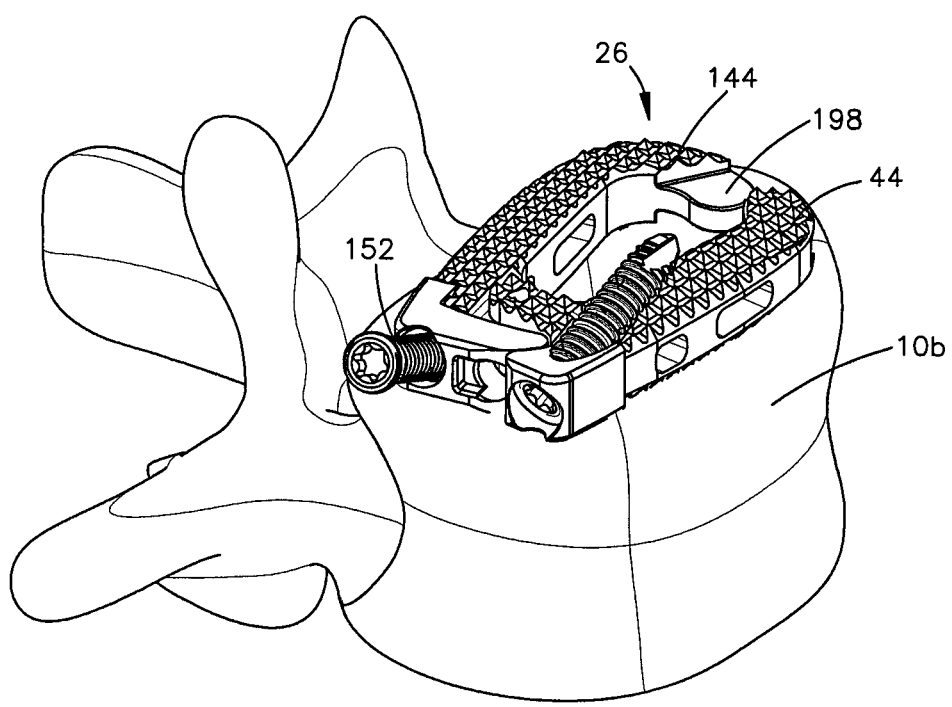
FIG. 3G is a side perspective view of a second fixation element being inserted into a second fixation element receiving aperture of the second body member of the implant shown in FIG. 3F.
Figure 3H:
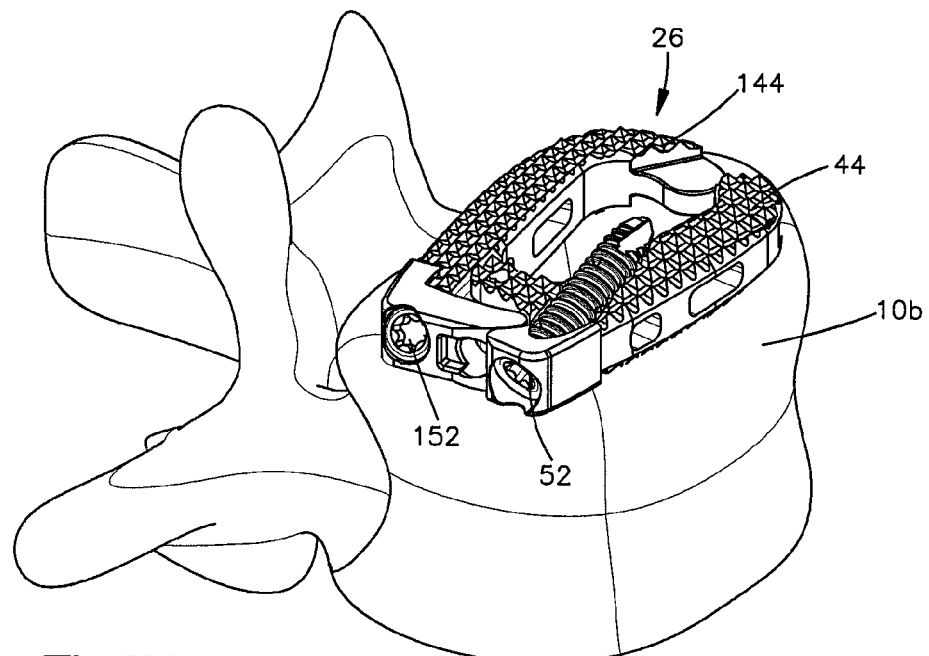
FIG. 3H is a side perspective view of the second fixation element fully inserted into the second fixation element receiving aperture of the implant so as to affix the second body member of the implant to the inferior vertebral body.
Figure 3I:
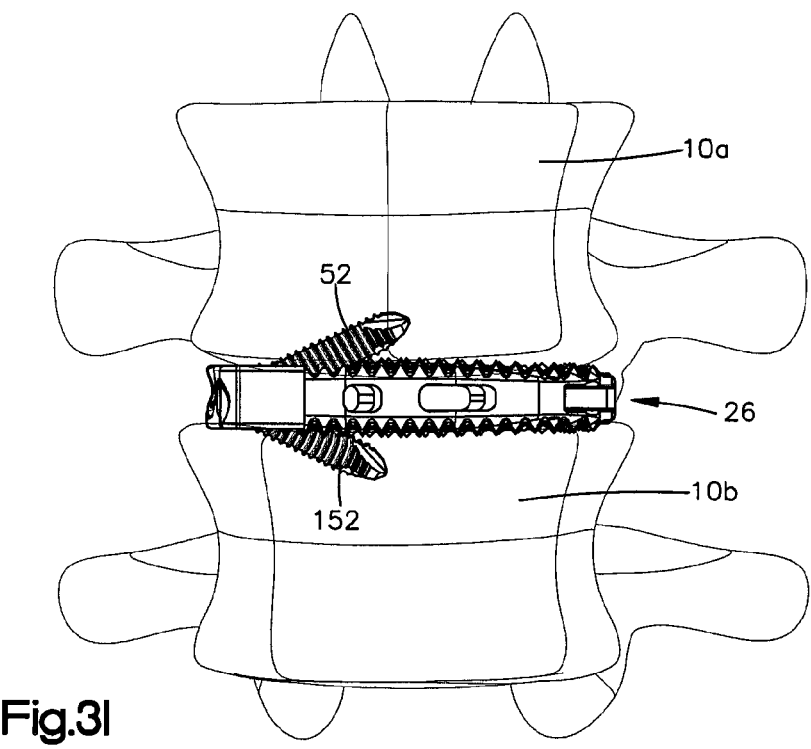
FIG. 3I is a side elevation view showing the implant of FIG. 3H affixed to the superior and inferior vertebrae.

Once the implant 26 has been expanded, the second bone screw 152 may be inserted through the fixation element receiving aperture 148 of the second body member 34 and into the inferior vertebral body 10b, as shown in FIGS. 3G and 3H. Once the bone screw 152 has been affixed to the inferior vertebral body 10b, the implant 26 will be securely affixed to the vertebrae such that the first and second body members won't rotate or otherwise change their orientation, as shown in FIG. 3I.

It should be understood that the second body member 34 may be affixed to the inferior vertebral body 10b first, rather than affixing the first body member 30 prior to expanding the implant 26 to its expanded configuration. Furthermore, it should be understood that the implant 26 may be expanded to its expanded configuration prior to any of the first and second body members 30 and 34 being affixed to the superior and inferior vertebral bodies 10a and 10b. Therefore, the implant 26 may be expanded unilaterally by affixing one of the body members 30 and 34 prior to expansion, or bilaterally by expanding the implant 26 prior to affixing any of the body members 30 and 34 to the vertebrae. In either case, due to the expansion of the cavity 200 between the first and second body members 30 and 34, the cage or at least the cavity 200 may be filled with filler material (e.g. autologous, allograft bone, bone filler substitute) after implantation of the implant 26. This could be achieved through injection or packing of the material into the cavity 200.

In another embodiment and in reference to FIGS. 4A and 4B, the implant 26 may be expanded by inserting an expandable element 110 directly into the cavity 200. In this embodiment, there may be no need for the channel 102. For example, as shown in FIGS. 4A and 4B, the expandable element may be inserted through the holding aperture 154 and into the cavity 200. Once positioned, the expandable element 110 may be activated or otherwise expanded and force the body members 30 and 34 to rotate relative to each other about the hinge 38. It should be understood, however, that the expandable element 110 may be inserted directly into the cavity 200 without going through the holding aperture 154.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present disclosure.

What is claimed is:

1. An expandable interbody fusion implant for insertion between two adjacent vertebrae and that is configured to move from an initial configuration to an expanded configuration, the implant comprising:
   a first body member having a first body having a distal portion and a proximal portion and an upper surface configured to engage a first vertebra and a lower surface configured to engage a second vertebra and a first plate coupled to the proximal portion of the first body;
   a second body member pivotally coupled to the first body member about a pivot axis, the second body member having a second body having a distal portion and a proximal portion and an upper surface configured to engage the first vertebra and a lower surface configured to engage the second vertebra and a second plate coupled to the proximal portion of the second body, wherein the first and second body members are pivotally coupled at the proximal portion of the first and second bodies;
   wherein the first and second plates each define a fixation element receiving aperture that is configured to receive a bone screw to selectively affix the first body member to the first vertebra and the second body member to the second vertebra; and
   a channel that extends at least partially through at least one of the first and second bodies, the channel configured to receive an inflatable balloon,
   wherein the second body member is configured to be adjacent the first body member, such that expansion of the inflatable balloon biases at least one of the first and second body members away from the other in a direction transverse to the pivot axis, thereby causing the implant to move from the initial configuration to the expanded configuration.

2. The implant according to claim 1, wherein the first body member has a first mating feature, and the second body member has a second mating feature that is configured to engage the first mating feature when the implant is in the initial configuration.

3. The implant according to claim 2, wherein the channel extends through the first body and into the first mating feature.

4. The implant according to claim 2, wherein the first mating feature is a recess, and the second mating feature is a protrusion that is capable engaging the recess when the implant is in the initial configuration.

5. The implant according to claim 1, wherein the channel extends through the entire length of the first body.

6. The implant according to claim 1, wherein the first plate defines a curved surface and the second plate defines a curved surface that corresponds to the curved surface of the first plate so as to allow the first plate to move relative to the second plate when the implant is being expanded to the expanded configuration.

7. The implant according to claim 1, wherein the fixation element receiving apertures are angled.

8. The implant according to claim 7, wherein the second plate further defines a holding aperture that is configured to be engaged by an insertion tool to thereby couple the implant to the insertion tool.

9. The implant according to claim 8, wherein the holding aperture is aligned with the channel, such that both the channel and the holding aperture are configured to receive the inflatable balloon.

10. The implant according to claim 1, wherein the implant while in the initial configuration has a first footprint width, and while in the expanded configuration has a second footprint width that is greater than the first footprint width.

11. The implant according to claim 1, wherein (i) the first and second body members each include a joint that defines an aperture, and (ii) the apertures are aligned and receive a pin such that the first body member and the second body member are each capable of rotating about the pin.

12. The implant according to claim 1, wherein the channel is nonlinear.

13. The implant according to claim 1, wherein the first and second bodies are cage bodies.

14. An expandable interbody fusion implant system that is configured to be inserted into an intervertebral space defined between a superior vertebral body and an inferior vertebral body, the implant being configured to have an initial configuration and an expanded configuration, the implant comprising:
   a first body member configured to be braced against a vertebral surface, the first body member including a first elongate cage body having a distal portion and a proximal portion, the first elongate cage body defining superior and inferior bone engaging surfaces that are configured to engage the superior and inferior vertebral bodies, respectively, the first elongate cage body having a free end at the distal portion and a first plate coupled to the proximal portion; and a second body member pivotally coupled to the first body member about a pivot axis, the second body member including a second elongate cage body having a distal portion and a proximal portion, the second elongate cage body defining superior and inferior bone engaging surfaces that are configured to engage the superior and inferior vertebral bodies, respectively, the second elongate cage body having a free end at the distal portion and a second plate coupled to the proximal portion, wherein the first and second body members are pivotally coupled at the proximal portion of the first and second elongate cage bodies, wherein the first and second plates each define a fixation element receiving aperture that is configured to receive a bone screw to selectively affix the first body member and the second body member to one of the respective superior and inferior vertebral bodies, wherein the implant is configured to receive an expandable element, such that when the expandable element is expanded at least one of the first body member and the second body member pivots with respect to other body member so as to move at least the free end of the second body member relative to the free end of the first body member and expand the implant to the expanded configuration.

15. The implant system according to claim 14 wherein the fixation element receiving aperture on the first and second plates are each angled in a different direction toward either the superior or inferior vertebral body.

16. The implant system according to claim 15, wherein the second plate further includes an aperture sized to receive the expandable element.

17. The implant system according to claim 14, further comprising a channel that extends through the first cage body, the channel configured to receive the expandable element.

18. The implant system according to claim 17, wherein the free end of the first cage body defines a recess and the free end of the second cage body defines a protrusion that engages the recess when the implant is in the initial configuration.

19. The implant system according to claim 14, wherein the first plate defines a curved surface and the second plate defines a curved surface that corresponds to the curved surface of the first plate so as to allow the first plate to move relative to the second plate when the implant is being expanded to the expanded configuration.

20. The implant system according to claim 15, wherein the first angled fixation element receiving aperture is configured to receive a bone screw that engages the superior vertebral body and the second angled fixation element receiving aperture is configured to receive a bone screw that engages the inferior vertebral body.

21. The implant system according to claim 14, wherein the second body member further defines a holding aperture that is configured to be engaged by an insertion tool to thereby couple the implant to the insertion tool.

22. The implant system according to claim 14, further comprising an inflatable balloon that functions as the expandable element.

23. The implant system according to claim 14, wherein the first elongate cage body is spaced apart from the second elongate cage body such that a cavity is defined between the first and second elongate cage bodies, the cavity configured to receive the expandable element.

24. The implant system according to claim 14, wherein the first body member and second body member are pivotally coupled such that only the second body member pivots relative to the first body member when the expandable element is expanded.

25. A method of implanting an intervertebral implant into an intervertebral space that is defined by a first vertebral body and an adjacent second vertebral body, the method comprising:

inserting an expandable implant into the intervertebral space, the implant comprising
a first body member having a first body having a first surface and an opposing second surface and a distal portion and a proximal portion, and a first plate defining a fixation element receiving aperture coupled to the proximal portion of the first body;
a second body member having a second body having a first surface and an opposing second surface and a distal portion and a proximal portion, and a second plate defining a fixation element receiving aperture coupled to the proximal portion of the second body;
wherein the first and second bodies are pivotally coupled together at the proximal portion of the first and second bodies about a pivot axis, and the implant having a first insertion width;

inserting the implant into the intervertebral space where the distal portions of the first and second bodies are the leading portions of the first and second body members to enter the intervertebral space;

positioning an expandable element within the implant;

expanding the implant in a direction that is substantially perpendicular to the pivot axis to a second width that is greater than the first width, and advancing a first bone screw through the fixation element receiving aperture of the first plate and into the first vertebral body and advancing a second bone screw through the fixation element receiving aperture of the second plate and into the second vertebral body and engaging the first surface of the first and second bodies with the first vertebral body and engaging the second surface of the first and second bodies with the second vertebral body.

26. The method according to claim 25 wherein the expandable element is an inflatable balloon and the expanding step is accomplished by inflating the inflatable balloon.

27. The method according to claim 26 further comprising inserting the implant into the intervertebral space by connecting an insertion tool into an insertion tool aperture on the second plate.

28. The method according to claim 27 wherein the inflatable balloon is positioned within the implant via the insertion tool aperture on the second plate.

29. The method according to claim 26, wherein one of the first and second body members defines a channel and the inflatable balloon is inserted through the channel.

30. The method according to claim 26, wherein the bone screws are inserted at an angle to the pivot axis.

31. The method according to claim 26, wherein when the balloon is inflated one of the first and second bodies pivots relative to the other body while one of the first and second bodies remains stationary.

32. The method according to claim 26, further comprising inserting a fixation element through the fixation element receiving aperture of the second body member prior to inflating the balloon, such that upon inflation of the balloon, the first body member rotates relative to the second body member.

\* \* \* \* \*